United States Patent [19]

Uetsuki et al.

[11] Patent Number: 5,348,858
[45] Date of Patent: Sep. 20, 1994

[54] MONOCLONAL ANTIBODY SPECIFIC FOR HUMAN INTERLEUKIN-1β AND METHOD FOR DETECTION OF BIOLOGICALLY ACTIVE HUMAN INTERLEUKIN-1β

[75] Inventors: Setsuyoshi Uetsuki; Osamu Sato; Yasuo Nakayama; Yoshikatsu Hirai, all of Tokushima, Japan

[73] Assignee: Otsuka Pharmaceutical Co., Ltd., Tokyo, Japan

[21] Appl. No.: 815,875

[22] Filed: Jan. 6, 1992

Related U.S. Application Data

[63] Continuation of Ser. No. 414,336, Sep. 29, 1989, abandoned.

[30] Foreign Application Priority Data

Oct. 1, 1988 [JP] Japan ................ 63-248535

[51] Int. Cl.$^5$ ............ G01N 33/53; C12N 5/20; C07K 15/28; C12P 21/08
[52] U.S. Cl. .................. 435/7.1; 435/240.27; 435/172.2; 435/70.21; 530/388.23; 436/548
[58] Field of Search ......... 530/388.23; 435/240.27, 435/7.1, 70.21, 172.2; 436/548

[56] References Cited

U.S. PATENT DOCUMENTS 4,935,343  6/1990  Allison et al. ............... 435/7.7

FOREIGN PATENT DOCUMENTS 0187991  7/1986  European Pat. Off. .
0245052  11/1987  European Pat. Off. .

OTHER PUBLICATIONS

Scapigliati J. Leukocyte Biology 42(5):544 1987.
Odum Scand. J. Immunol. 27:405, 1988.
Boraschi et al. Progress in Leukocyte Biology vol. 8, Powanda et al. Eds. Alan R. Liss Inc. 1988.
March Nature 315:641, 1985.
Kenney et al. J Immunology 138:4236, 1987.
Wunderlich J. Leukocyte Biology 42(5) 594, 1987.
Wunderlich Progress in Leukocyte Biology vol. 8, Powanda et al. Eds. Alan R. Liss Inc. 1988.
Kipps IN Handbook of Expt'l. Immunology vol. 4, pp. 108.1–108.9, Herzenberg et al., Blackwell Sci. Publ. 1986.
Dunn, S. D., Analytical Biochemistry 157:144–153, 1986.

*Primary Examiner*—Paula K. Hutzell
*Attorney, Agent, or Firm*—Sughrue, Mion, Zinn, Macpeak & Seas

[57] ABSTRACT

The present invention provides a monoclonal antibody characterized in that the antibody has specific reactivity on human IL-1β, and a process for producing the antibody. The invention also provides a method for detection of biologically active human IL-1β.

3 Claims, 3 Drawing Sheets

MONOCLONAL ANTIBODY SPECIFIC FOR HUMAN INTERLEUKIN-1β AND METHOD FOR DETECTION OF BIOLOGICALLY ACTIVE HUMAN INTERLEUKIN-1β

This is a continuation of application Ser. No. 07/414,336 filed 29 Sep. 1989, now abandoned.

The present invention relates to an antibody against interleukin-1β (IL-1β), and more particularly to a novel monoclonal antibody against human IL-1β which antibody makes it possible to immunologically purify, determine or neutralize IL-1β.

It is known that human IL-1 is produced not only by macrophages and monocytes but also by various other cells and exhibits diversified molecular forms and biological activities. Presently two kinds of human IL-1 are known which differ in isoelectric point, i.e., IL-1α and IL-1β. The primary structures of these interleukins are also known (Nature, 315, p.641 (1985); J. Exp. Med., 164, p.237 (1986), etc.).

Extensive research has been conducted on applications of IL-1 as a drug, while attention has been directed to the determination of IL-1 especially in clinical samples, for example, for research on immunodeficiencies and abnormal immune responses and for the clinical diagnosis of such abnormalities.

At present, bioassay is known as a technique for determining IL-1. With this method, IL-1 is determined in terms of the activity thereof in test samples. The method is inefficient and low in accuracy and involves a need to consider the presence of a factor interfering with the measurement. Additionally, the method has the serious drawback of failing to distinguish IL-1α and IL-1β since these interleukins exhibit the same activity.

An object of the present invention is to provide a novel antibody against human IL-1β.

Another object of the present invention is to provide an antibody against human IL-1β for use in a novel immunoassay method which is adapted to determine human IL-1β as distinguished from human IL-1α and to selectively determine only IL-1β having biological activity.

Another object of the present invention is to provide an antibody against human IL-1β which is usable for various diseases involving abnormal production of IL-1β, to inhibit (neutralize) the activity of IL-1β.

Still another object of the present invention is to provide a technique for producing the above antibody.

The present invention provides a monoclonal antibody against human IL-1β characterized in that the antibody has specific reactivity with human IL-1β, and a process for producing the antibody.

The use of the antibody of the present invention provides a novel method of immunoassay adapted to determine with high sensitivity, high accuracy and ease human IL-1β having biological activity as distinguished from IL-1α.

Since the antibody of the invention is specific for human IL-1β, the use of the antibody provides a means for purifying human IL-1β specifically, for example, by affinity chromatography.

Figure 1:
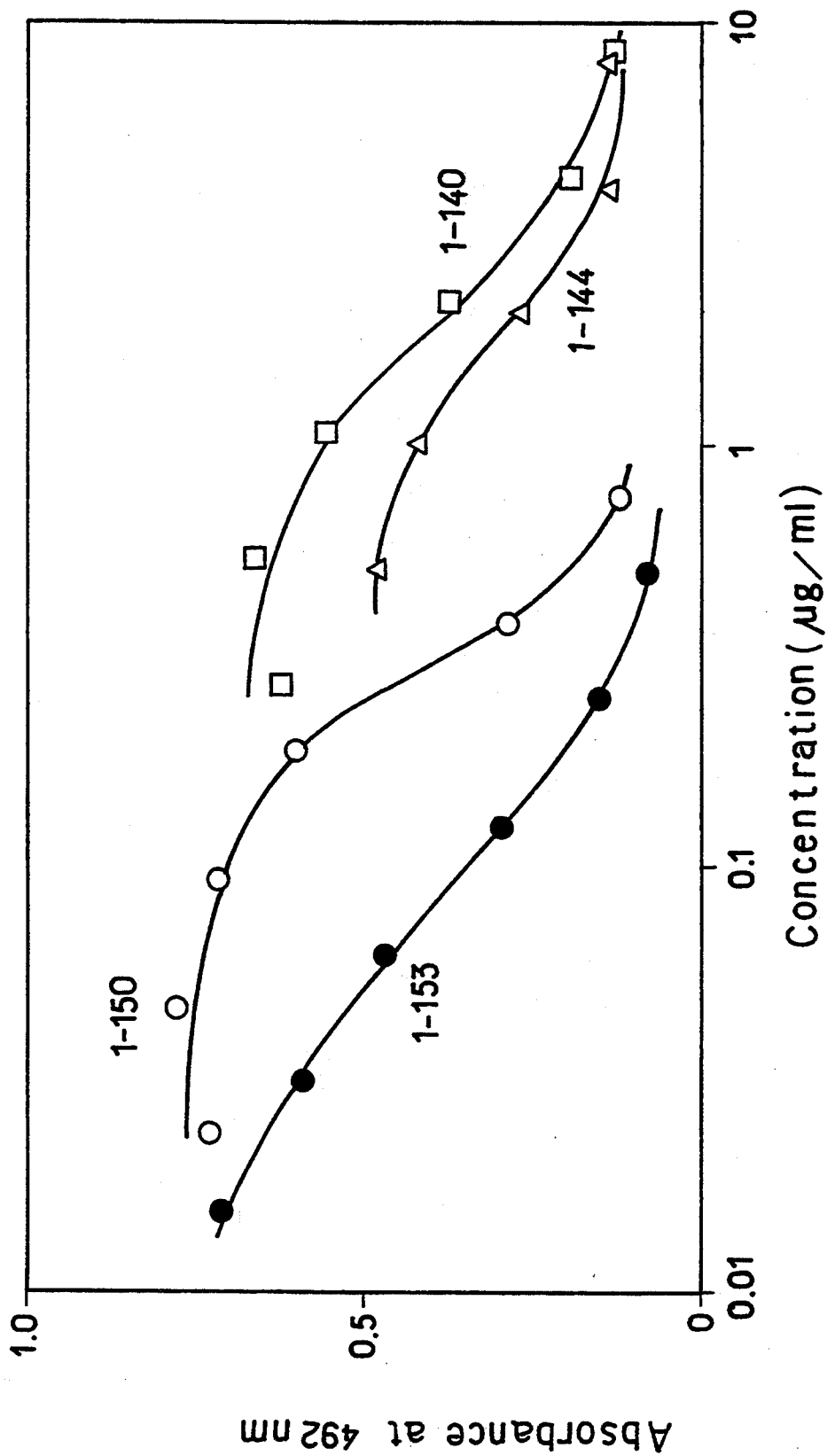
FIG. 1 depicts the degree of competition between labelled IL-1β and polypeptides thereof, as noted, for binding with solid phase-bound GOM43-4.

The antibodies of the present invention include an antibody of the type having activity to neutralize the biological activity of human IL-1β. Whereas abnormal production of IL-1β is involved in diseases such as chronic articular rheumatism, thyroiditis, hepatitis, nephritis and like chronic inflammatory diseases, arterial sclerosis, Kawasaki disease and like angitis, disseminated intravascular coagulation and blood cancer, the antibody of this type is useful for inhibiting or neutralizing the enhanced biological activity of IL-1β due to the abnormal production thereof. Thus, the antibody provides a drug which is very valuable for treating these diseases.

The antibody of the present invention can be produced utilizing human IL-1β as an immunogen. Stated more specifically, the present antibody can be produced by preparing hybridoma cells from plasmacytes (immunocytes) of a mammal immunized with the immunogen and plasmacytoma cells of a mammal, preparing from the hybridoma a selected clone which produces the desired antibody recognizing human IL-1β and cultivating the clone.

The human IL-1β serving as the immunogen for use in the above process is not limited specifically. Useful as such is any of a culture supernatant containing human IL-1β derived in vitro by a known method, purified sample thereof, human IL-1β prepared by gene recombination techniques and synthetic peptides having a portion of the amino acid sequence thereof.

Although the mammal to be immunized with the immunogen is not limited specifically, it is desirable to select a suitable animal in view of the compatibility of the plasmacyte with the plasmacytoma cell to be fused therewith. Generally, mice and rats are advantageously usable.

The mammal is immunized by a usual method, for example, by intravenously, intracutaneously, subcutaneously or intrapertitoneally administrating the immunogen thereto, more specifically, by administrating the immunogen (along with a usual adjuvant when desired) to the animal several times every 2 to 14 days at a total dose of, for example in the case of a mouse, about 100 to about 500 μg/mouse. It is desired that the immunocytes to be used be spleen cells removed from the animal about 3 days after the final administration of the immunogen.

Plasmacytoma cells of mammals useful as the other host cells to be fused with the immunocytes are various known ones, such as P3 (P3/x63-Ag8) [Nature, 256, 495–497 (1975)], P3-U1 [Current Topics in Microbiology and Immunology, 81, 1–7 (1978)], NS-1 [Eur. J. Immunol., 6, 511–519 (1976)], MPC-11 [Cell, 8, 405–415 (1976)), SP2/0 (Nature, 276, 269–270 (1978)], FO [J. Immunol. Meth., 35, 1–21 (1980)], x63.6.5.3. [J. Immunol., 123, 1548–1550 (1979)], S194 [J. Exp. Med., 148, 313–323 (1978)], R210 of rats [Nature, 277, 131–133 (1979)] and like myeloma cells.

The fusion reaction between immunocytes and plasmacytoma cells can be conducted by a known method, such as the method of Milstein et al. (Meth. Enz., Vol. 73, p.3 (1981)). More specifically, the fusion reaction is conducted in a usual medium in the presence of a usual fusion promoting agent such as polyethylene glycol (PEG) or haemagglutination virus of Japan (HVJ). To achieve an improved fusion efficiency, auxiliary agents such as dimethyl sulfoxide can be added to the medium when required. The immunocyte and the plasmacytoma are used in a usual ratio. For example, immunocytes are used generally in about 1 to about 10 times the amount of plasmacytoma cells. Examples of media useful for the fusion reaction are those usually used for proliferating plasmacytoma cells, such as RPMI-1640 medium and MEM medium, and other media which are generally used for cultivating such cells. It is usually desirable to use the medium without serum supplements, such as fetal calf serum (FCS). For fusion, predetermined quantities of immunocytes and plasmacytoma cells are mixed thoroughly together in the medium, and a solution of PEG, for example, having an average molecular weight of about 1000 to about 6000 preheated to about 37° C., is admixed with the medium usually to a concentration of about 30 to about 60 W/V %. Subsequently, a suitable medium is admixed with the suspension from time to time, followed by centrifuging to remove the supernatant. Repetition of this procedure affords the desired hybridoma.

The desired hybridoma obtained is selected by cultivation in a usual selection medium such as HAT medium (containing hypoxanthine, aminopterin and thymidine). The cultivation with the HAT medium is conducted for a period of time, usually several days to several weeks, sufficient to extinguish the cells (e.g. unhybridized cells) other than the desired hybridoma cells. The hybridoma cells obtained are then subjected to the usual limiting dilution method to search for clones producing the desired antibody.

The desired antibody-producing clones can be screened by various methods which are generally used for detecting antibodies, such as the ELISA method (Engvall, E., Meth. Enz., 70, 419–439 (1980)), plaque method, spot method, agglutination method, Ouchterlony method and radioimmunoassay (RIA). The immunogen is usable for this purpose.

The hybridoma which produces the desired monoclonal antibody recognizing human IL-1$\beta$ can be subcultured in a usual medium and can be preserved in liquid nitrogen for a prolonged period of time.

The desired antibody can be collected from the culture supernatant of the hybridoma in the usual manner, or from the ascites fluid of a mammal compatible with the hybridoma by administering the hybridoma thereto for proliferation. The former method is suitable for preparing the antibody with a high purity, while the latter method is suited to quantity production of the antibody.

The antibody thus obtained can be further purified by a usual method such as salting out, gel filtration or affinity chromatography.

The monoclonal antibody of the invention prepared in this way has specific reactivity to human IL-1$\beta$.

The antibody of the invention which is of the type having activity to neutralize the biological activity of human IL-1$\beta$ is well suited to the specific determination of human IL-1$\beta$ having biological activity. Further the antibody of the type having such neutralizing activity, especially the antibody of the type which recognizes the site on the IL-1$\beta$ molecule participating in the binding to an IL-1 receptor, is suited to application to the aforementioned diseases involving abnormal production of IL-1$\beta$.

The present invention provides a monoclonal antibody specific to human IL-1$\beta$. The use of the antibody of the invention provides a method of immunoassay which is exceedingly high in determination sensitivity and excellent in specificity and which is therefore adapted to accurately determine human IL-1$\beta$ having biological activity and present at a very low concentration in samples such as clinical samples.

The present invention will be described in greater detail with reference to the following examples, which nevertheless in no way limit the invention.

EXAMPLE 1

Preparation of the Present Antibody and its Characterization

Human [Ser$^{71}$] IL-1$\beta$ (Seikagaku, 58, No.8, p.840 (1986); EPO No.187991) prepared by gene recombination techniques was administered intraperitoneally to a BALB/c mouse at a dose of 1 to 10 $\mu$g every day for 4 weeks. Three to four days after the final immunization, cells were fused by the conventional method (see, for example, Meth. Enz., 73, p.3 (1981)). For cell fusion, the immunized spleen cell and the myeloma cell (NS-1, Eur. J. Immunol., 6, 511–519 (1976)) were used in the ratio of 5:1 using polyethylene glycol (PEG-1500).

The hybridoma cells were selected with HAT medium. The resulting supernatant was tested by enzyme immunoassay using a 96-well microplate coated with the above human IL-1$\beta$ and peroxidase-labeled goat anti-mouse immunoglobulin antibody (product of E. Y. Lab.) to detect cells producing the desired antibody against human IL-1$\beta$.

Through repeated cloning by the limiting dilution method, a clone producing the desired antibody was obtained.

The clone (hybridoma producing the antibody of the invention) has been deposited with the designation "Anti OCT-43 producing hybridoma cell (GOM43-4)" and deposition number FERM BP-2565 deposited 1 Oct. 1988 in the Fermentation Research Institute, Agency of Industrial Science and Technology, MITI 1-3, Higashi 1-chome, Tsukuba-shi, Ibaraki-ken, 305 Japan.

The antibody of the invention (hereinafter referred to as "GOM43-4") obtained from the clone has the following characteristics.

(1) Subclass of the Antibody

The subclass of the antibody determined with use of a mouse antibody subclass detecting kit (product of Bio-Rad) was IgG$_1$ kappa.

(2) Antibody Production Level

The amount of IgG in the culture supernatant was about 40 $\mu$g/ml when hybridoma cells were grown to the highest density.

(3) EIA Titer

The EIA titer determined by the following method was 2000.

Human IL-1$\beta$ adjusted to 200 ng/ml was placed into the wells of a 96-well microplate in an amount of 50 $\mu$l/well and allowed to stand overnight at 4° C. The plate was washed with PBS-Tween 20, and a diluted culture supernatant of the hybridoma was placed into the wells (50 $\mu$l/well), followed by reaction at 4° C. overnight and washing. Further peroxidase-labeled anti-mouse immunoglobulin (product of Cappel Laboratories, X2000) was placed into the wells in an amount of 50 μl/well to effect reaction similarly. After washing, the activity of bound enzyme was determined by colorimetry using O-phenylenediamine as a substrate. The reciprocal of the dilution ratio of the culture supernatant with $OD_{492}=0.5$ was taken at the EIA titer.

(4) Molecular Weight

The hybridoma was cultured intraperitoneally in a mouse, and the ascites fluid was purified to produce $IgG_1$ with an IgG purifying kit (MOPS Kit, product of Bio-Rad). The product was $1.7 \times 10^2$ kd in molecular weight. (The sum of molecular weights of heavy chains and light chains obtained by SDS-PAGE was taken as the molecular weight of the antibody.)

(5) Cross Reactivity

The procedure (3) was repeated using human IL-1α adjusted to 20 μg/ml in place of human IL-1β. The resulting optical density was not different from the blank value which was determined similarly without using IL-1. This indicates that the antibody of the invention exhibits no cross reactivity with human IL-1α.

(6) Neutralizing Activity

This activity was determined in terms of the ability of the antibody to inhibit IL-1β-mediated cytotoxic activity for A375 melanoma cells in vitro (GIF activity, Gann Monograph on Cancer Research, 34, 155 (1988)).

GOM43-4, the protein content of which was calculated by the UV method, was diluted with a medium to 100 μg/ml. The serial 2-fold dilutions were performed on a 96-well microplate using 50 μl/well of the culture medium. IL-1β adjusted to 40 units/ml was placed into the wells in an amount of 50 μl/well. Finally, a suspension of human melanoma A375 cells adjusted to $2 \times 10^4$ cells/ml was placed into the wells in an amount of 100 μl/well (final concentration of IL-1β: 10 units/ml). The mixture was incubated in an incubator at 37° C. in the presence of 5% $CO_2$ for 4 days and the anti-GIF activity of GOM43-4 was determined.

It was found that 2.5 μg of GOM43-4 was needed to reduce the GIF activity of IL-1β from 10 units to 1 unit.

(8) Determination of Binding Site

In the same manner as used for preparing human IL-1β (EPO No.187991), the following fragments of human IL-1β were prepared.

Fragments 1-153: human IL-1β polypeptide
1-150: polypeptide comprising the amino acids No.1 to No.150 in human IL-1β
1-144: polypeptide comprising the amino acids No.1 to No.144 in human IL-1β
1-140: polypeptide comprising the amino acids No.1 to No.140 in human IL-1β
4-153: polypeptide comprising the amino acids No.4 to No.153 in human IL-1β
7-153: polypeptide comprising the amino acids No.7 to No.153 in human IL-1β
17-153: polypeptide comprising the amino acids No.17 to No.153 in human IL-1β

To E. coli expressing each of human IL-1β and the above fragments was added 600 μl of 50 mM Tris buffer (pH 8.0) containing 25 mM of EDTA and 0.1% of lysozyme. The mixture was shaken and then allowed to stand in ice water for 15 minutes. To the mixture was further added 500 μl of 150 mM Tris buffer (pH 8.0) containing 0.3% Triton X100 and 190 mM EDTA, followed by shaking and then by centrifugation. The supernatant was diluted to fiftyfold with PBS-0.1% BSA to obtain a sample solution, which was subjected to an inhibition assay in the following manner.

The antibody of the invention adjusted to 10 μg/ml was placed into a 96-well microplate in an amount of 100 μl/well and allowed to stand at 4° C. overnight. After washing the plate with water, BSA was applied to the plate to prevent nonspecific adsorption and the plate was washed with water. The sample solution was placed into the wells in an amount of 100 μl/well, followed by reaction at room temperature for 2 hours. IL-1β (30 ng/ml) labeled with biotin was further placed into the wells in an amount of 100 μ/well and allowed to stand at 4° C. overnight. The plate was then washed with PBS-Tween 20, and peroxidase-labeled streptavidin (product of Bethesda Research Lab., X1000) was placed into the wells in an amount of 100 μl/well for reaction. After washing, the activity of the bound enzyme was determined by colorimetry using o-phenylenediamine as a substrate.

Figure 2:
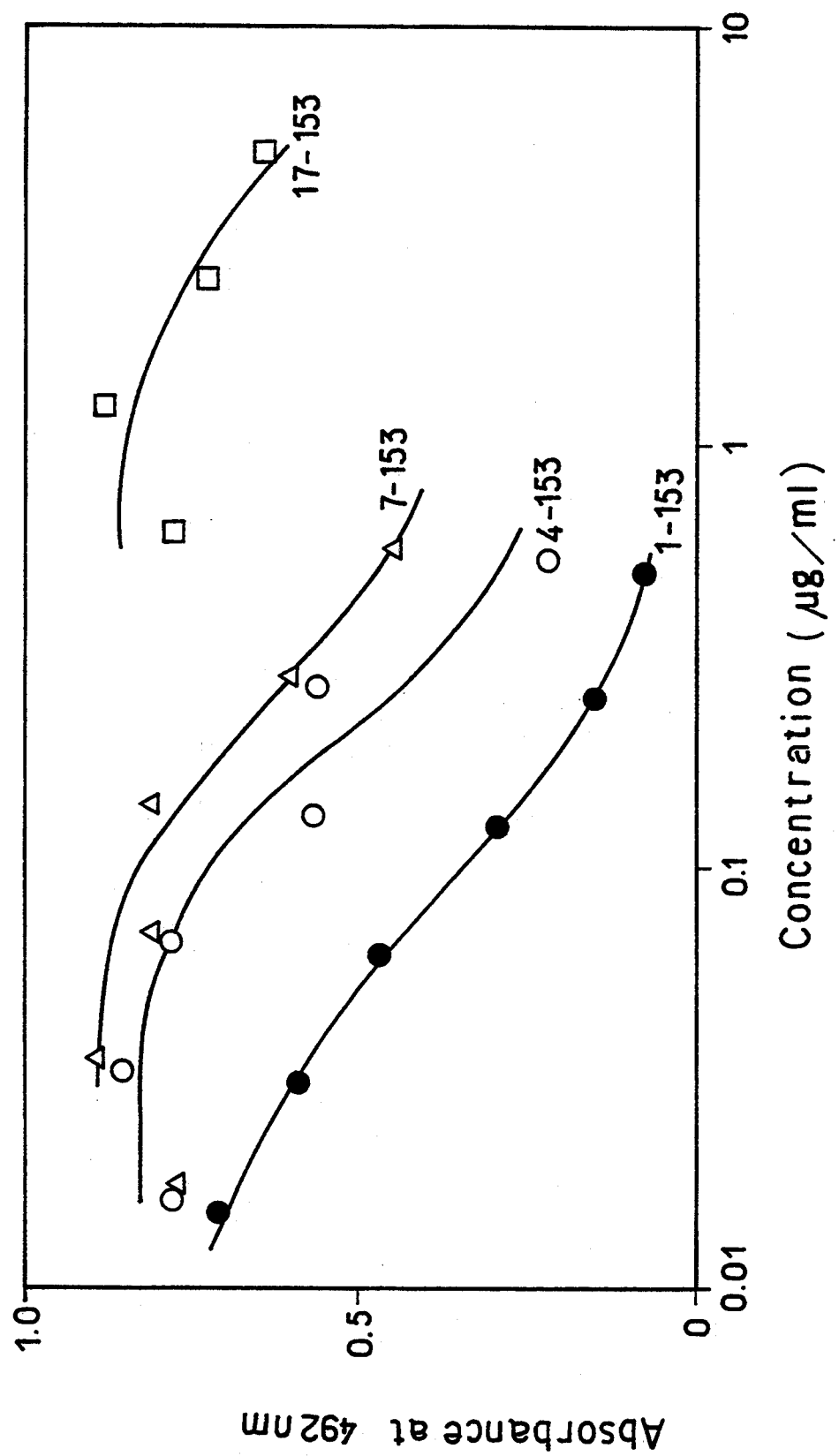
FIG. 2 depicts the degree of competition between labelled IL-1β and polypeptides thereof, as noted, for binding with solid phase-bound GOM43-4.

The result is shown in FIGS. 1 and 2, in which the concentration of polypeptide is plotted as abscissa, and the absorbance at 492 nm as ordinate. These diagrams show how the polypeptides inhibit binding of biotin-labeled IL-1β to the antibody of the invention.

Based on the reactivity of the various peptides as shown in FIGS. 1 and 2, it is reasonable to conclude that the antibody of the invention recognizes the conformation formed from the N and C-termini of human IL-1β.

EXAMPLE 2

ELISA System of Present Antibody (1) Sensitivity in ELISA System

The present antibody (GOM43-4) adjusted to 10 μg/ml was placed into the wells of 96-well microplate in an amount of 100 μl/well and allowed to stand at 4° C. overnight. After washing the plate with water, 1% BSA-5% FCS/PBS was applied to the plate (400 μl/well) for blocking to prevent nonspecific adsorption, followed by washing with water. The sample solution diluted with 0.1% BSA/PBS was placed into the wells in an amount of 100 μl/well and allowed to stand at 4° C. overnight, followed by washing with PBS-Tween 20. Rabbit anti-IL-1β antibody (5 μg/ml) was then placed into the wells (100 μl/well) and allowed to stand at room temperature for 2 hours. After washing the plate with PBS-Tween 20, peroxidase-labeled goat anti-rabbit IgG antibody (product of Bio-Rad, X20000) was placed into the wells (100 μl/well) to effect reaction at room temperature for 2 hours. After washing the plate, the activity of bound enzyme was determined by colorimetry using O-phenylenediamine as a substrate.

Based on the determination sensitivity for the sample concentration with an absorbance ($OD_{492}$ nm) of 0.1, the sensitivity of the present antibody for IL-1β was 80 pg/ml.

The sensitivity determination of the antibody for [$Ser^{71}$] IL-1β checked in the same manner as above was comparable to the above result.

(2) Correlation with Biological Activity

[Ser$^{71}$] IL-1β adjusted to 0.2 mg/ml (with 20 mM phosphate buffer, pH 7.0) was heated at 50°, 55°, 60° or 65° C. for 0 to 24 hours. The solutions thus treated were tested for sensitivity in ELISA system by the procedure (1) above and also for GIF activity by the procedure of Example 1, (6) to establish the correlation therebetween.

Figure 3:
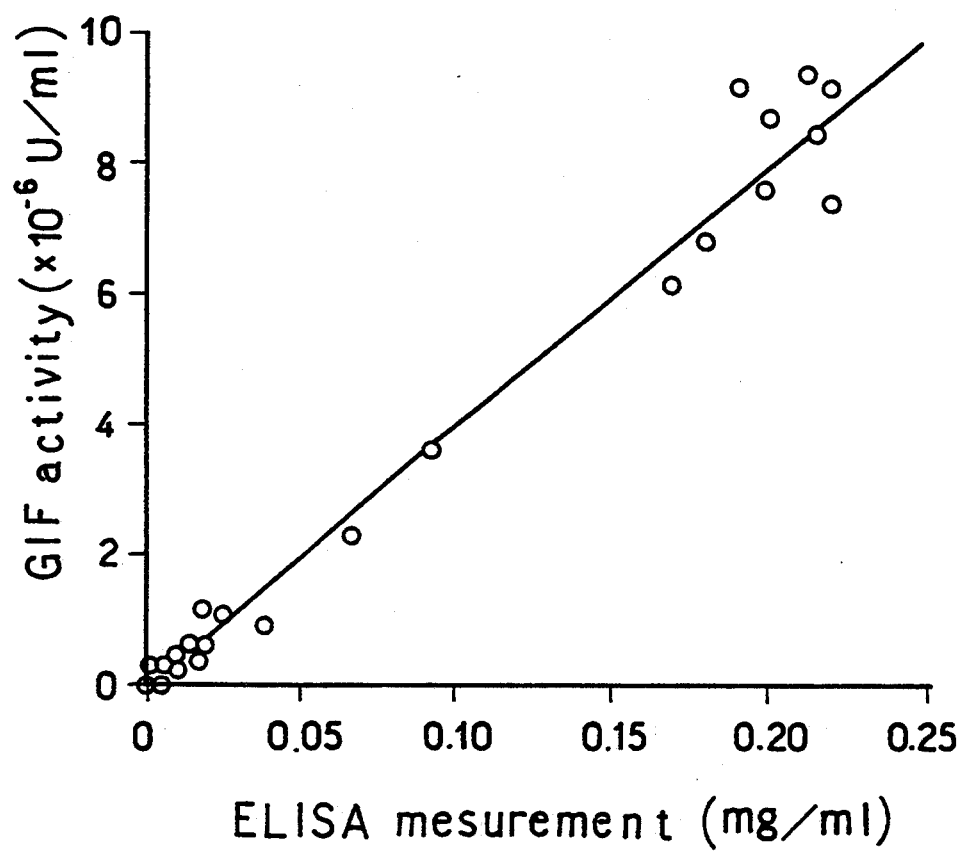
FIG. 3 depicts the biologic activity of heat treated IL-1β, expressed as GIF activity, relative to the immunoreactivity thereof using a GOM43-4 ELISA.

The result is given in FIG. 3, in which the measurement (mg/ml) in the ELISA system is plotted on the abscissa vs. the GIF activity measurement (x $10^{-6}$ U/ml) on ordinate to show the correlation.

The correlation coefficient calculated from the diagram was 0.988.

In the same manner as above, the present antibody was checked for sensitivity in the ELISA system as correlated with the biological activity of IL-1β. The result was comparable to the above result.

We claim:

1. Monoclonal antibody 1β GOM43-4 produced by hybridoma cell line FERM BP-2565.

2. A hybridoma cell line, FERM BP-2565, that produces the monoclonal antibody of claim 1.

3. An immunoassay method for detecting biologically active human interleukin-1β which comprises the steps of:
   (a) contacting a sample suspected of containing human interleukin-1β with a monoclonal antibody as defined in claim 1 in order to form an immune complex; and
   (b) determining the presence of said immune complex.

* * * * *